US00PP25773P3

(12) United States Plant Patent
Schoone

(10) Patent No.: US PP25,773 P3
(45) Date of Patent: Aug. 4, 2015

(54) ***PHALAENOPSIS* ORCHID PLANT NAMED 'FLOR168625'**

(50) Latin Name: *Phalaenopsis hybrida*
Varietal Denomination: FLOR168625

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 120 days.

(21) Appl. No.: 13/986,272

(22) Filed: Apr. 18, 2013

(65) Prior Publication Data

US 2013/0291245 P1 Oct. 31, 2013

Related U.S. Application Data

(60) Provisional application No. 61/638,199, filed on Apr. 25, 2012.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

(56) References Cited

U.S. PATENT DOCUMENTS

PP14,328 P2 * 12/2003 Plate ..... Plt./311

OTHER PUBLICATIONS

The Royal Horticultural Society 2014, Search the International Orchid Register, retrieved on Oct. 1, 2014, retrieved from the Internet at <http://apps.rhs.org.uk/horticulturaldatabase/orchidregister/orchiddetails.asp?ID=86866> pp. 3-4.*

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'FLOR168625' particularly characterized by flowers which are yellow/green with some purple/red stripes with a purple/red labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'FLOR168625'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'FLOR168625'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'FLOR168625' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'FLOR168625' originated from a cross made by the inventor in 1999 in Strengweg, Heemskerk, The Netherlands. The female or seed parent is the *Phalaenopsis* cultivar designated 'Lawrence', unpatented. The male or pollen parent is the *Phalaenopsis* cultivar designated 'Little Gem Stripes', unpatented. The new *Phalaenopsis* 'FLOR168625' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'FLOR168625', which in combination distinguish this *Phalaenopsis* as a new and distinct cultivar:

1. flowers which are yellow/green with some purple/red stripes and a purple/red labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'FLOR168625', the female parent 'Lawrence' has yellow flowers and the male parent 'Little Gem Stripes' has pink striped colored flowers, whereas the flowers of 'FLOR168625' are yellow/green with a purple/red labellum.

Presently, a commercial cultivar to which 'FlOR168625' can be meaningfully compared is 'Exotic Moon' (Patented, U.S. Plant Pat. No. 14,328). The flowers of 'FLOR168625' are smaller than the flowers of 'Exotic Moon'. Also are there more flowers on a raceme of 'FLOR168625' and the plant height of 'FLOR168625' is smaller than 'Exotic Moon'.

BRIEF DESCRIPTION OF THE PHOTOGRAPHS

The accompanying photographs illustrate the overall appearance of the new *Phalaenopsis* 'FLOR168625' showing the colors as true as is reasonably possible with colored reproductions of this type. Colors in the photographs may differ slightly from the color values cited in the detailed botanical description, which accurately describe the color of 'FLOR168625'.

DETAILED BOTANICAL DESCRIPTION

Figure 1:
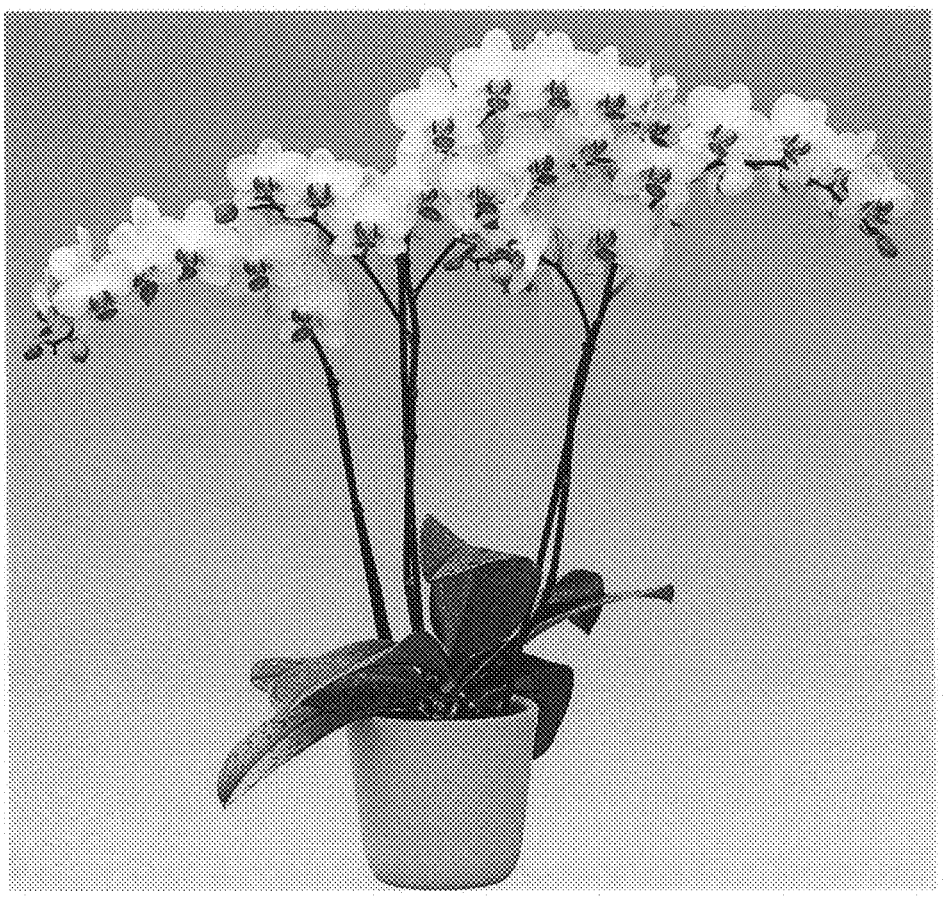
FIG. 1 shows a side view perspective of a typical flowering plant of 'FLOR168625' in a 12 cm pot, at 16 months of age.

The new *Phalaenopsis* cultivar 'FLOR168625' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'FLOR168625' as grown in a greenhouse in Strengweg, Heemskerk, The Netherlands, under conditions which closely approximate those generally used in commercial practice. Initially, the ideal temperature to grow plants of 'FLOR168625' is 27° C. during the day and at night. Then, during the flowering phase of 'FLOR168625', the ideal growing temperature is 20-22° C. during the day and 18° C. at night. Light levels for growing 'FLOR168625' are a minimum of 5,000 lux and a maximum of 10,000 lux. A balanced fertilizer with level of 200 ppm N, 87 ppm P, 168 ppm K is applied. Duration of growth of 'FLOR168625' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'FLOR168625' plants described is 12 months after potting.

Classification:

*Botanical.—Phalaenopsis hybrida.*

Parentage:

*Female or seed parent.—Phalaenopsis* cultivar designated 'Lawrence', unpatented.

*Male or pollen parent.—Phalaenopsis* cultivar designated 'Little Gem Stripes', unpatented.

Propagation:

*Type.*—Tissue culture.

*Rooting habit and description.*—Fleshy; approximately 4 mm-7 mm wide and green in color (RHS 191B and 143D); freely branching. It takes 12 weeks for plants growing in tissue culture to initiate roots.

Plant:

*Size at maturity.*—Height: about 40 cm to 60 cm. Spread: about 35 cm to 45 cm.

*Growth habit.*—Small; green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is pointy and asymmetric.

*Texture (upper & underside).*—Smooth and leathery.

*Pubescence.*—None.

*Mature leaf length.*—About 15 to 30 cm.

*Mature leaf width.*—About 6 cm.

*Mature leaf thickness.*—About 1.5 mm.

*Mature leaf color.*—Upper side: green (RHS 137B). Under side: green (RHS 146A and RHS 137D). Edges, veins and a haze of purple (RHS N79A) and greyed/purple (RHS 187A).

*Leaf base.*—Acute.

*Margin.*—Entire.

*Venation.*—Pattern: parallel. Color of midvein: upper side: green (RHS 137A). Under side: purple (RHS N79A) and greyed/red (RHS 178A).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 3.

*Number of flowers per raceme.*—About 5 to 18.

*Length.*—About 30 to 60 cm.

*Peduncle*.—Diameter: about 3 mm. Strength: strong. Aspect: upright. Texture: glabrous and smooth. Color: grey/brown (RHS 199A) and grey/green (RHS 197A).

*Buds*.—Height (from base to tip): about 18 mm. Diameter (at midpoint): about 9 mm to 17 mm. Shape: egg-shaped. Color: main color is yellow/green (RHS 146B) which runs out into RHS 145A/RHS 144C.

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
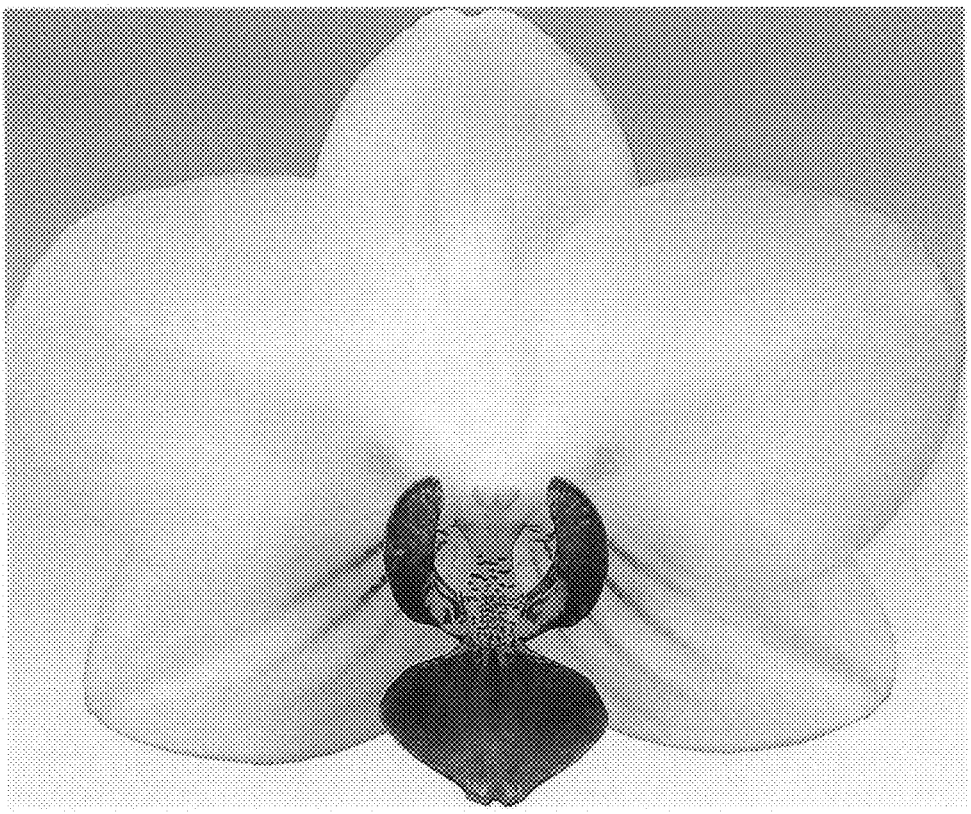
FIG. 2 shows a close-up view of a typical flower of 'FLOR168625'.
Figure 3:
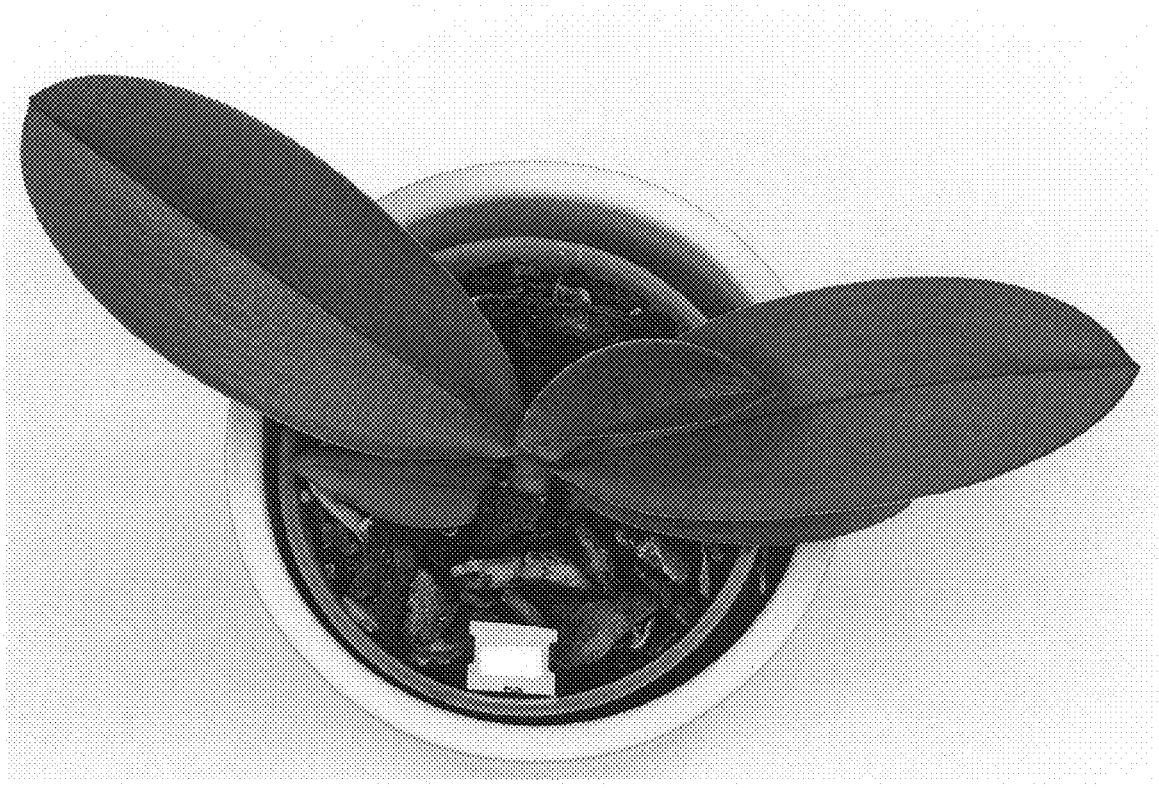
FIG. 3 shows a close-up view of the typical leaves of 'FLOR168625'.

*Flower*.—Rate of opening: Flowers fully opened about 2 to 3 days after petal and sepal separation. Orientation at opening: slanted upward and outward. Shape: Typical shape of *Phalaenopsis* orchid: see FIG. 2. Size (of single bloom): Height: about 40 mm to 70 mm. Diameter: about 60 mm to 80 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 32 mm. Width: about 30 mm. Texture: Upper surface: smooth and satiny. Under surface: smooth and satiny. Color (when fully opened): upper side: main color is yellow/green (RHS 150D). At the base some white (RHS NN155C). Close to base a purple mark (RHS N78B). Under side: main color is yellow/green (RHS 150D) with at the base some white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is rhombic with a bump and a rib on it. Margin: entire and weakly undulate. Apex: oval. Midlobe: Length: about 18 mm. Width (not flattened): about 13 mm. Lateral lobe: Length: about 17 mm. Width (not flattened): about 12 mm. Texture: Upper and under surface: smooth and satiny. Color (when fully opened): Midlobe: upper surface: main color is red/purple (RHS 61A). At the base little white (RHS NN155C) and some yellow/orange (RHS 14B). Same yellow/orange also on the sides. Close to the cirrhi some purple (RHS N78A) and some white (RHS NN155C) Under side: in the center white (RHS 155C) from base to end. Sides at the base are red/purple (RHS 71B) and yellow/orange (RHS 14B). The rest of the underside is red/purple (RHS 72B). Lateral lobes: upper surface: at the base white (RHS NN155A). Small yellow edge on the side (RHS 14B) which runs into red/purple (RHS 61A) and purple (RHS 72A). In the center some red/purple (RHS 59A) and yellow (RHS 14B) stripes. Under side: white (RHS NN155A) with purple (RHS 72A) and yellow (RHS 15A) on the sides. Cirrhi: small (about 2 mm). Color: white (RHS NN155C) and purple (RHS N78A). Pestle (Callosities): Length: about 5 mm. Width (not flattened): about 4 mm. Depth of tube created by lateral lobes of labellum: about 5 mm. Color: main color is yellow (RHS 6B) with some white (RHS NN155C) and red/purple spots (RHS 61 A).

*Sepals*.—Arrangement: Outer whorl comprises 3 sepals, one dorsal and two lateral sepals. Overall shape: elliptical and weakly cupped. Margin: entire and weakly undulate. Length: about 35 mm. Width: about 24 mm. Apex: dorsal: oval; lateral: oval and little pointy. Texture: Upper and under surface: smooth and satiny. Color (when fully opened): upper surface: dorsal and lateral: main color is yellow/green (RHS 150D) at the base white (RHS NN155C). dorsal has some faded red/purple veins (RHS 71 B). Lateral has red/purple spots and stripes (RHS 61A). Under surface: dorsal and lateral: main color is yellow/green (RHS 150D) which fades into RHS 145C. At the base some white (RHS NN155C). At the lateral sepals some red/purple stripes (RHS 71B).

*Pedicel*.—Length: about 25 mm to 35 mm. Diameter: about 3 mm. Texture: glabrous and smooth. Color: turns from yellow/green (RHS 146C) into RHS 145C to white (RHS 155C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 7 mm. Diameter: about 5 mm. Color: white (RHS 155C).

*Pollinia*.—Quantity: two. Diameter: about 1 mm. Color: yellow/orange (RHS 23A).

*Ovary*.—Length: about 3 mm. Diameter: about 2 mm. Color: white (RHS NN155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'FLOR168625', as illustrated and described herein.

* * * * *